United States Patent [19]

Karlson

[11] Patent Number: 5,167,927
[45] Date of Patent: Dec. 1, 1992

[54] MONITOR FOR OZONE, HYDROGEN PEROXIDE AND OTHER GASES IN FLUIDS

[76] Inventor: Eskil L. Karlson, 4634 State St., Erie, Pa. 16509

[21] Appl. No.: 429,628

[22] Filed: Oct. 31, 1989

[51] Int. Cl.⁵ ............................................. G01N 27/04
[52] U.S. Cl. .................................. 422/90; 422/94; 422/95; 73/25.01; 73/25.03; 374/10
[58] Field of Search .................... 422/90, 94, 95; 73/25.01, 25.03, 23.2; 374/10, 45

[56] References Cited
U.S. PATENT DOCUMENTS

| | | | |
|---|---|---|---|
| 2,899,281 | 8/1959 | Olmer | 422/96 |
| 4,668,635 | 5/1987 | Forster | 422/94 |
| 4,920,792 | 5/1990 | DiFoggio | 73/153 |

Primary Examiner—Robert J. Warden
Assistant Examiner—Laura E. Collins

[57] ABSTRACT

This monitoring invention is an improvement over the ozone ($O_3$) and hydrogen peroxide ($H_2O_2$) monitoring systems that are now commercially used.

The manner in which this monitor measures the gas, or a gas dissolved in a liquid, is by measuring the heat energy that is released when the material to be measured is catalyzed. The detector measures the heat produced when, for example, ozone is reduced to oxygen or the hydrogen peroxide is reduced to oxygen and water by a catalytic action. This heat energy is collected and measured. The higher the temperature, the higher the concentration.

4 Claims, 5 Drawing Sheets

MONITOR FOR OZONE, HYDROGEN PEROXIDE AND OTHER GASES IN FLUIDS

This new ozone or hydrogen peroxide measuring instrument is small, is quite simple, and can either be made portable or be designed into a large complex system; furthermore it is inexpensive to manufacture.

BACKGROUND OF THE INVENTION

One of the most difficult problems when working with ozone or hydrogen peroxide is the measurement of its exact concentration in a moving gas. The problem becomes more severe if either or both the pressure and temperature of the gas are changing. There are a number of instruments commercially available that will measure ozone but they are complicated, expensive, difficult to calibrate and have a long time constant. These commercial instruments are difficult to design into a system and generally can not be built to be portable.

It should be pointed out that U.S. Pat. No. 3,153,577 of 1964 teaches the use of a DC bridge circuit for measuring ozone concentration when the detector is a thermistor. This patent does not measure or control flow, temperature or pressure.

U.S. Pat. No. 4,409,183 of 1983 covers a method to measure ozone in water. However, different dissolvable salts will produce errors in the measurements.

The U.S. Pat. No. 2,899,281 teaches the use of a catalyst coated thermistor employed in a bridge, as does U.S. Pat. No. 3,153,577. Neither of these patents takes the pressure of their samples into account in their measurements and calculations, nor does either patent employ a heat sink with or at their thermistors. By not taking both temperature and pressure into the concentration calculations, they can not measure an ozone concentration of 2 parts per million with any accuracy or confidence.

The U.S. Pat. No. 3,464,797 of 1966 teaches the measuring of ozone by a charcoal catalyst held in a tube. This is fine, but this patent has not taken into account either the gas temperature or its pressure and it does not teach how to control its gas or how it controls or measures the time constant. This system's sensitivity is also low.

The common problem with most of the commercial ozone monitoring instruments available is that they do not cover a broad enough range and are to slow to respond. For example, in the wood pulp industry, the need is for an instrument with a fast time constant that will measure ozone concentration and also be the detector to control the total bleaching system. In this case, the ozone is (in its gas phase operating at a temperature from 5 to 25 degrees centigrade at a concentration up to 20%) employed as a bleaching agent on wood pulp. The ozone is administered quickly so as not to destroy the fibers. It is therefore necessary to quickly know the ozone concentration at different temperatures and pressures. The problem is measuring and following any change in concentration at high concentrations at different pressures and at changing temperatures. These measurements must be done continuously, as part of the system, with an instrument having a short time constant of less than 0.25 seconds.

Another point, is that most of the available instruments for monitoring ozone or hydrogen peroxide are not meant to be portable. The need, when working with ozone or hydrogen peroxide, is for a portable instrument that can be used to sniff out where an $O_3$ or an $H_2O_2$ leak may occur. This portable instrument should be sensitive, (less than 1 part per million full scale), have a short time constant with an accuracy of plus or minus 2% or less, and be battery powered. It should also be equipped with a long intake tube that can be used to reach out to check for leaks around flanges and valves, for example, in a city's drinking water purification systems employing ozone as a sterilant or in a waste water disinfection plant. In all cases, both monitors, the stationary installed ozone system monitor or the hand held portable model, should be completely automatic, need little or no calibration, be simple and need only minor servicing.

SUMMARY

For the past 20 years, science has been looking for an inexpensive, simple monitor that could be relied on to measure and control ozone concentration in hospital sterilizer units and in city water supply systems that employ $O_3$ as the sterilant. The methods of testing employed now are expensive and cumbersome. The need for a hydrogen peroxide monitor for $H_2O_2$ as a gas or in its liquid state is also great, for $H_2O_2$ is finding uses in hospitals as a disinfectant and sterilant and in many areas it is used as a powerful oxidant.

An interesting fact about this new method of gas concentration monitoring is that a number of different gases can be detected and their concentration measured by this same technique. The catalysts chosen would be specific for the gas or liquid measured, and its heat released by catalytic action, would be measured as an indicator of its concentration.

DETAILED DESCRIPTION OF INVENTION

FIG. 1 is a diagram of a system for detecting ozone concentration.

FIG. 2 includes front, back and side views of the detectors.

FIG. 2b is an enlarged edge view of the part of one of the detectors circled by dotted lines in FIG. 2a;

Figure 1:
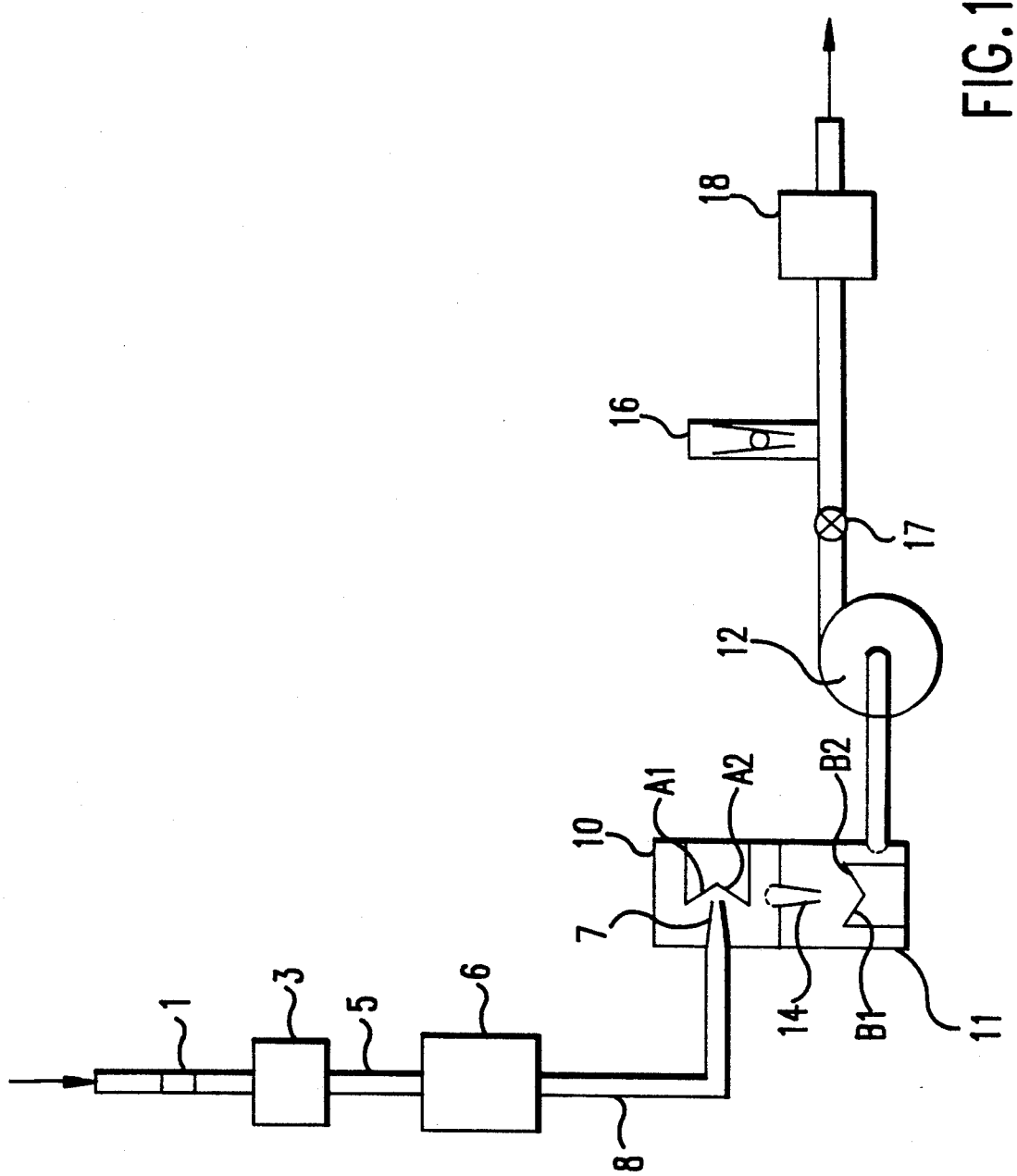
Figure 2C:
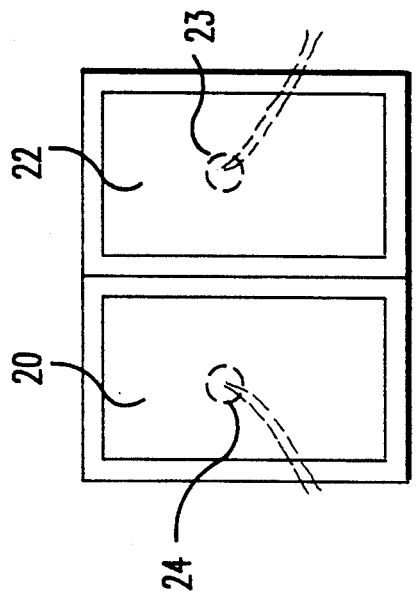
FIG. 2c is a front view of the detectors.
Figure 2D:
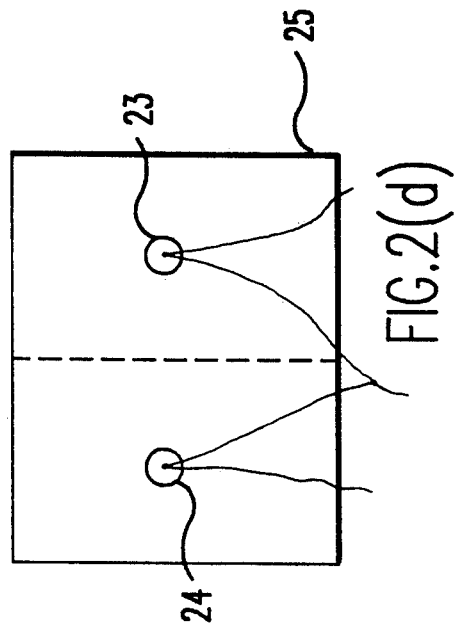
FIG. 2d is a back view of the detectors.
Figure 2A:
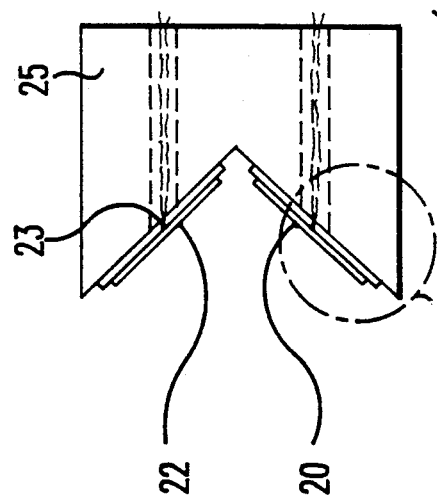
FIG. 2a is a side elevation of the thermal detectors.
Figure 2B:
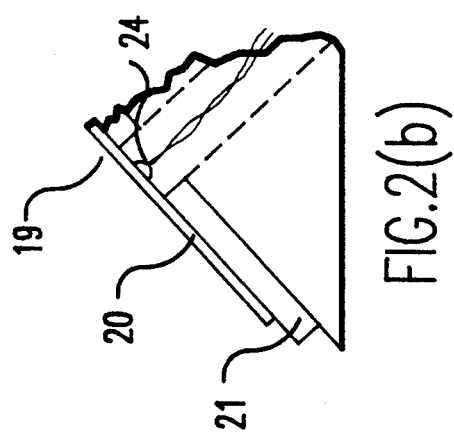

This invention can be employed as an ozone monitor in the following manner. The sample is picked up by line "5," as shown in FIG. 1. This sample passes through a dust collector "1" and through the gas heater "3." It then is drawn through a nitrous oxide filter at "6" which is only included in the circuit when nitrous oxide may be present in the gas monitored. Some nitrous oxide will form if air is used to supply oxygen for the ozone generator. Filter "6" is omitted if oxygen is employed as a raw gas for the ozone generator. Heater "3" may also be omitted if the gas monitored is relatively dry with a humidity less than 20%.

After the $O_3$ gas passes through filter at "6", it continues through "8," into chamber "10," through nozzle "7," at which point the gas increases in velocity. The gas impinges on thermal detector areas "A1," and "A2." The gas then is drawn from chamber "10" to a second same sized chamber "11" by pump "12." As the gas is passed into chamber "11", hitting the second pair of thermal detectors "B1" and "B2," its velocity has again increased as it passes through jet "14."

The ozone gas detection is accomplished by measuring the resistance difference between the active and compensating thermistors "A1" and "A2," "B1" and "B2," in the "10" and "11" chambers. The active area of "A1" and "B1" is coated with an ozone catalyst. The compensating area is coated with a non oxidizing insulator. The ozone is catalyzed, as it hits the active areas "A1" and "B1." The catalyst converts the ozone back into oxygen releasing heat. This heat energy changes the resistance of the active area thermistor which has the property of changing resistance at a negative rate of 5% per degree centigrade. The ozone concentrations of the pumped gas sample is thus electronically measured, being the resistance difference of the two flakes in each chamber. The sample flow is controlled by electronic flow meter "16" and valve at "17." It is important that the sample flow is constant for each sample. The instrument's sensitivity and time constant is dependent on the velocity of sample flow through the instrument, its electronic time constant and its thermal time constant. The calibration is measured and recorded at a set operating controlled flow at 90% of each range. Four other calibration points 10%, 20%, 40%, and 60% are also measured to check instrument linearity. Before the sample leaves the instrument, for safety, it is completely catalyzed at point "18" to rid the gas of any remaining ozone.

The electronics and the thermal detectors are the same for both the portable and the permanently installed system. The ozone detection system is simply the electronic measurement of the heat energy that is released when the ozone is converted back into oxygen. This is actually a calorimetric measuring instrument.

With a first detection method, the gas to be monitored is impinged on two monitoring plates, in both FIGS. 1 and 2. Number "20" acts as the active plate, its temperature increases by the heat of converting the ozone to oxygen and the second plate, number "22" is acting as a compensating plate in FIG. 2, its temperature only following ambient or the temperature of the incoming sample. The active plate number "20" is covered with activated copper oxide or other ozone catalyst, "19," which will convert ozone to oxygen. The catalyst "19," is a fine lightweight powder coating covering the active copper or silver plate "20." The thermal collecting plates "20" and "22" are both light weight, thin, less than 1/10 of one millimeter, each having an area of 25 to 250 square millimeters. The compensating plate "22" is bare, not covered by any catalyst.

It is only coated with a thin nonoxidizable nonactive coating. The compensating plate is the same size and has the same weight as the total weight of the active plate with its catalyst. The temperature of the copper plates are both measured by a short time constant thermistor beads "23" and "24" or a micro thermocouple implanted on the back of each of the copper plates. The backs of both copper plates are both coated with an insulating material that attaches them to the heat sink "25," FIG. 2. This film is used as the thermal and electrical insulator. This plastic film is 1/100 of one millimeter or less thick. This film between the metal plates "20" and "22" and their heat sink "25," and the weight of the metal plates "20" and "22" plus the thermal detector beads weight, sets the time constant of ozone detection.

Normally, the longer the time constant, the better the sensitivity.

It should be stated that the heat sinks are made of a metal such as copper or silver that have a high thermal conductivity and high thermal capacity. It should be noted that all metals except the stainless steel chambers of this instrument are coated with a gold flash to control oxidation.

Figure 3:
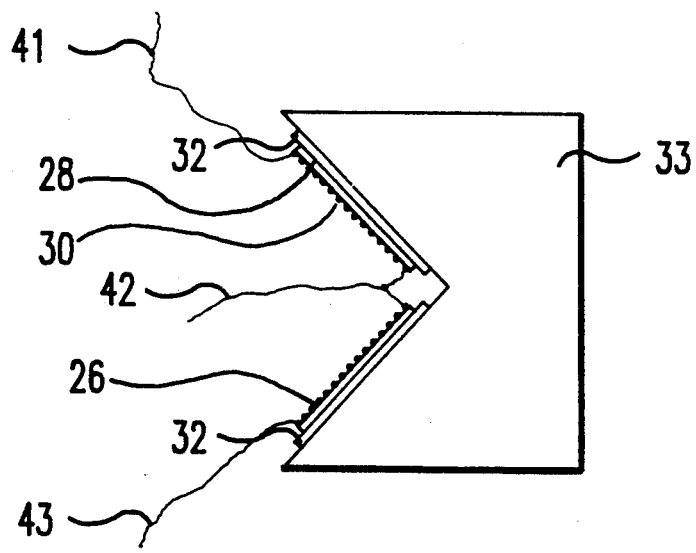
FIG. 3 is a view of a modification of the detectors.

A second detector design can also be used, FIG. 3. This ozone detector design employs two thermistor flakes instead of the copper plates and thermistor beads as shown in FIG. 2. The active flake "26," in FIG. 3, is coated with a thin coat of activated copper oxide ozone catalyst or any other catalyst that will catalyze ozone to convert it to oxygen. The compensating flake "28" is coated but with an insulator material "30" having the same weight as the catalytic material. The compensating flake's coating will not act as a catalyst and can not be oxidized or chemically changed by the ozone. The thermistor flakes are thin sheets of thermistor material "type A" having an area of $5 \times 5$ mm or larger. Both the active thermistor and its compensator are attached over a thin plastic film, approximately 100 microns thick, "32," as shown in FIG. 3, to their metal heat sink "33" as shown in FIG. 3. This second model detector system has a faster time constant and is more sensitive than the detector described in FIG. 2, for its thermal losses are less; that is, less thermal loss between the catalyst and the thermal detector.

Figure 4:
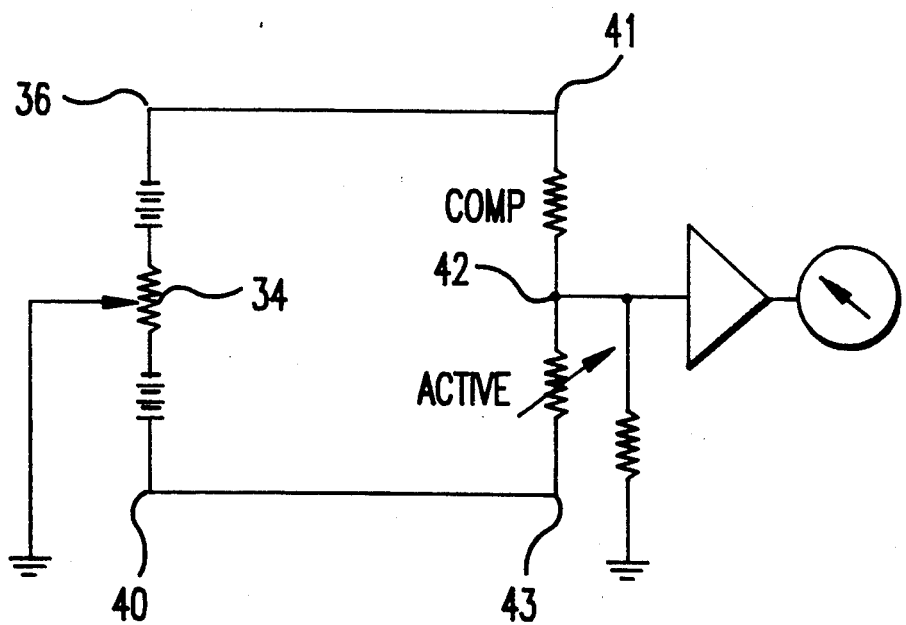
FIG. 4 is a bridge circuit used to measure the temperature of the detectors.
Figure 5:
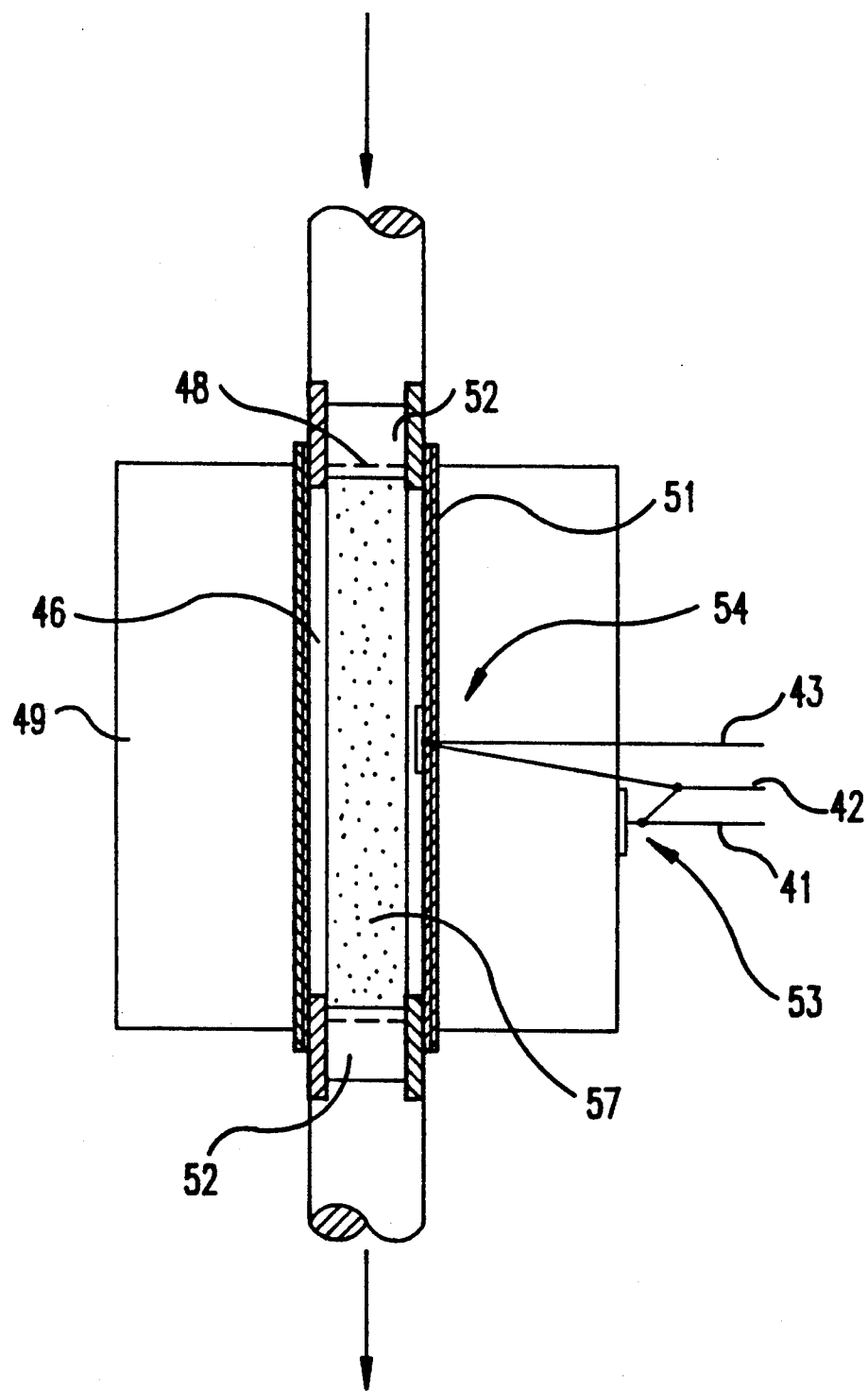
FIGS. 5 and 6 show modification of the detectors.
Figure 6:
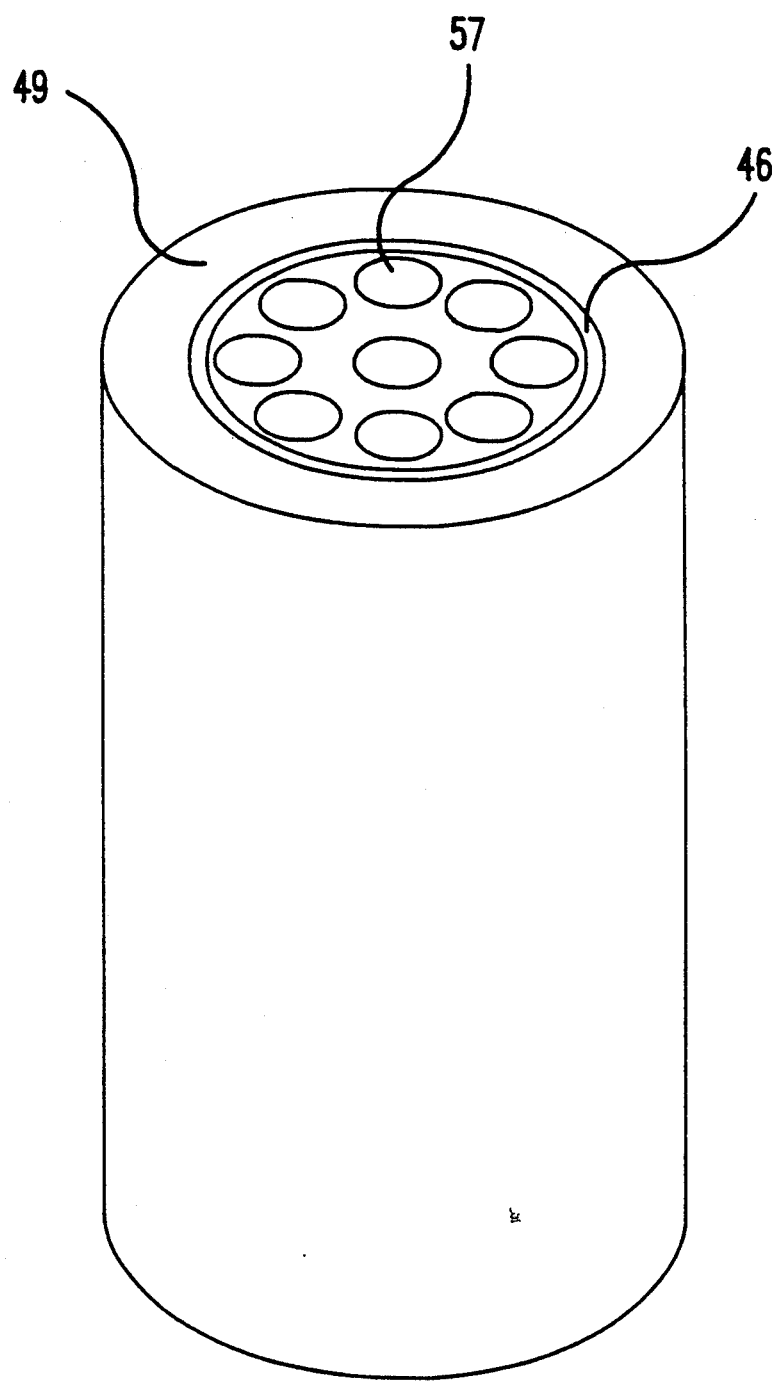

Two or more sets of detectors in chambers in succession can be used to produce large signals when measuring low concentrations of ozone as in FIG. 1. Each detector in the first and second chamber "10" and "11" is supplied with a pair of $5 \times 5$ millimeter or larger thermistor flakes mounted on a heat sink as shown in FIG. 3. In operation, the incoming gas jet strikes both thermistor flakes. Approximately 50% hit the active flake and 50% fall on the compensating flake. The detection of ozone is accomplished by having the active flake coated with a catalyst as shown in FIG. 3, converting the ozone to oxygen, releasing its binding energy in the form of heat as the ozone is converted to oxygen. The compensating flake is coated with polystyrene, Teflon, or an epoxy film that will not act as a catalyst or be oxidized. The higher the ozone concentration, the more energy will be released as heat. The hotter the active flake gets, the lower its resistance becomes. (Since the flakes employed have a 5% per degree centigrade negative resistance). The ozone concentration will only change the resistance of the active flake. The differential resistance change between the active and compensating flake is directly related to the amount of ozone concentration in the sample being measured. The active and compensating thermistors are parts of an electrical bridge, as shown in FIG. 4. Note placement of leads "41," "43" and signal lead "42" in FIG. 3 and in FIG. 4. (The same electronic configuration works for both FIG. 2 and FIG. 3). Any temperature change of cooling or heating by either the incoming gas flow or any ambient temperature change will not be seen as a signal inasmuch as both thermistors will follow the ambient temperature. A signal will only develop when the active thermistor is at a different temperature than its compensating thermistor.

During its use and operation, the instrument will read zero for an ambient temperature range from 40 degrees F. to 100 degrees F. with no ozone in the sample being monitored. The active and compensating thermistor resistance will both go up or down simultaneously as the ambient temperature changes, or if the temperature of the gas being monitored changes. No signal will appear because both the active and the compensating thermistor are matched in resistance and time constant. Both flakes (the active and compensating) were chosen to have the same resistance within less than 0.5% at 20 degrees Centigrade. Both thermistors (bead or flake) have a thermal negative resistance change value of 5% per degree Centigrade.

The start switch is also a part of the zeroing potentiometer. Resistor "34," in FIG. 4, will zero out any battery voltage change. This detector system can also be designed to operate on AC by feeding point "36" and point "40" with pulses in phase derived from a center tapped transformer with each side zener controlled.

An ozone monitor designed for system installation and continuous use, would also be designed to measure pressure, temperature and humidity. The sample read out could be reported as % concentration by weight or volume or as if the sample were at 20 degrees C. at room ambient pressure or whatever the system may require for control.

I claim:

1. A gas monitoring apparatus for measuring ozone or hydrogen peroxide concentration in a gas comprising means for directing a stream of said gas against matched thermally conducting plates on opposite sides of the axis of said stream and extending upstream at an acute angle to said axis, one plate carrying on its upstream side a coating including a catalyst for ozone or hydrogen peroxide and the other plate carrying on its upstream face a second coating equal to the first plate's, weight and thermal properties, but without the catalyst, and sensing means on the downstream side of each said plates for measuring the temperature of its plate and means for indicating the difference between said temperatures to indicate the concentration of ozone or hydrogen peroxide in said gas.

2. The apparatus of claim 1 further comprising a heat sink on the downstream side of said plates for equilizing the temperatures of said plates.

3. The apparatus of claim 2 plus insulation between said plates and said heat sink for varying the response time of the temperature indicators.

4. The apparatus of claim 1 in which the means for directing the gas against the plates comprises a nozzle directed toward the upstream side of said plates.

* * * * *